United States Patent [19]
Winter et al.

[11] Patent Number: 6,033,530
[45] Date of Patent: Mar. 7, 2000

[54] CONTINUOUS DISTILLATION OF THERMOLABILE MONOMERS

[75] Inventors: Manfred Winter, Dittelsheim-Hessloch; Jacques Dupuis, Ludwigshafen, both of Germany

[73] Assignee: BASF Aktiengesellschaft, Ludwigshafen, Germany

[21] Appl. No.: 08/816,735

[22] Filed: Mar. 14, 1997

[30] Foreign Application Priority Data

Jun. 5, 1996 [DE] Germany .......................... 196 22 674

[51] Int. Cl.[7] .............................. B01D 3/10; B01D 3/36; C07C 233/00
[52] U.S. Cl. ................... 203/70; 203/91; 203/94; 203/98; 564/216
[58] Field of Search .................... 203/52, 68, 70, 203/91, 94, 98; 159/47.1, DIG. 10, DIG. 16; 549/274, 216, 123, 197

[56] References Cited

U.S. PATENT DOCUMENTS 4,814,505  3/1989  Kroener et al. .......................... 564/216
4,990,222  2/1991  Aigner et al. .............................. 203/91

FOREIGN PATENT DOCUMENTS 0289069  12/1986  Japan .
0230155  9/1993  Japan .

*Primary Examiner*—Virginia Manoharan
*Attorney, Agent, or Firm*—Oblon, Spivak, McClelland, Maier & Neustadt, P.C.

[57] ABSTRACT

A process for the continuous distillation of thermolabile monomers under reduced pressure in a column includes

- feeding the thermolabile monomers in vapor or liquid form to the column,
- introducing an inert distillation aid which forms a heteroazeotrope with the thermolabile monomers into the vaporizer at the bottom of the column, but separately from the monomer feed, and vaporizing into there or feeding an emulsion of thermolabile monomers and an inert distillation aid into the vaporizer or into the column,
- condensing the azeotrope at the top of the column and separating it in a phase separator, taking off the thermolabile monomers and returning the distillation aid to the column or, if desired, working it up by distillation and
- taking off components having a higher boiling point than the thermolabile monomers from the bottom of the column.

7 Claims, No Drawings

CONTINUOUS DISTILLATION OF THERMOLABILE MONOMERS

The present invention relates to a process for the continuous distillation of thermolabile monomers under reduced pressure in a column.

EP-A-0 231 901 discloses a process for purifying N-vinylformamide by fractional distillation of the N-vinylformamide. N-vinylformamide is a thermolabile monomer and, according to the known process, is fractionally distilled in the presence of formamide under a pressure of 0.5 to 30 mbar in a column, with the distillation being controlled in such a way that the distillate comprises N-vinylformamide having a formamide content of from 0.1 to 15% by weight. This distillation process makes it possible to obtain monomer qualities from which homopolymers of N-vinylformamide having very high molar masses can be prepared. Although this process offers decisive advantages in terms of monomer quality compared with fractional distillation of N-vinylformamide in the absence of formamide, the N-vinylformamide thus produced still contains impurities in the ppm range. These impurites have not yet been identified, but they interfere in the polymerization because they lead to a limitation of the molar mass of the polymers.

The distillation of thermolabile monomers frequently results in formation of dissociation products which accumulate during the distillation and have an adverse effect on the course of the distillation. In some cases, it is even possible for blocking of the distillation column to occur. On the other hand, low-boiling dissociation products of thermolabile monomers can contaminate the distillate.

It is an object of the present invention to provide an improved process for the distillation of thermolabile monomers.

We have found that this object is achieved by a process for the continuous distillation of thermolabile monomers under reduced pressure in a column, by feeding the thermolabile monomers in vapor or liquid form into the column, introducing an inert distillation aid which forms a heteroazeotrope with the thermolabile monomers into the vaporizer at the bottom of the column, but separately from the monomer feed, and vaporizing into there or feeding an emulsion of thermolabile monomers and an inert distillation aid into the vaporizer at the bottom of the column or into the column, condensing the azeotrope at the top of the column and separating the distillation aid from the thermolabile monomer in a phase separator and returning the distillation aid to the column or, if desired, working it up by distillation and taking off components having a higher boiling point than the thermolabile monomers from the bottom of the column.

For the purposes of the present invention, thermolabile monomers are monoethylenically unsaturated monomers which decompose during distillation. The distillation of thermolabile monomers frequently results in the formation of impurities which, even in the ppm range, interfere in the polymerization of the distilled monomers. Such monomers include, for example, N-vinylcarboxamides. They can, for example, have a cyclic structure such as N-vinylpyrrolidone or substituted N-vinylpyrrolidones or they have an open-chain structure, for example as described by the formula below:

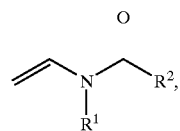

where $R^1$ and $R^2$ can be identical or different and are hydrogen or $C_1$–$C_6$-alkyl. Examples of monomers of this type are N-vinylformamide ($R^1=R^2=H$ in formula I), N-vinyl-N-methylformamide, N-vinylacetamide, N-vinyl-N-methylacetamide, N-vinyl-N-ethylacetamide, N-vinyl-N-methylpropionamide and N-vinylpropionamide. The process of the present invention is particularly suitable for producing high-purity N-vinylformamide.

The thermolabile monomers are preferably fed to the column in liquid form. In the preferred embodiment of the process of the present invention, an inert distillation aid which forms a heteroazeotrope with the thermolabile monomers is introduced into the vaporizer at the bottom of the column, but separately from the monomer feed. However, it is also possible to make a finely dispersed emulsion from the thermolabile monomers and an inert distillation aid and pump it into the vaporizer at the bottom of the column or into the column. An emulsion of thermolabile monomers and an inert distillation aid is obtained, for example, by applying high shear forces to the starting components. Such an emulsion can be produced, for example, by means of an Ultra-Turrax. The mixture then has sufficient stability to be pumped into the vaporizer or into the column.

The energy necessary for the thermal separation process within the column is introduced into the system by vaporizing the distillation aid by means of a vaporizer at the bottom of the column. The temperature in the bottom of the column is, for example, from 50 to 140° C., preferably from 80 to 110° C., with the pressure at the top of the column during the distillation being, for example, from 0.1 to 100 mbar. Constituents having boiling points higher than the thermolabile monomers collect in the liquid phase in the column. They are continuously discharged together with part of the distillation aid from the bottom of the column and are continuously replaced by addition of fresh distillation aid. The distillation aid can be measured in gaseous or liquid form into the vaporizer or, if desired, in liquid form into the column. If an emulsification apparatus is available, the thermolabile monomers to be purified together with the inert distillation aid can be processed to form an emulsion and the emulsion can be pumped into the vaporizer or into the column. However, the thermolabile monomers and the inert distillation aids are preferably pumped separately into the column or into the vaporizer. Based on one part by weight of the thermolabile monomers, use is made, for example, of from 0.01 to 10 parts by weight, preferably from 0.5 to 2 parts by weight, of an inert distillation aid which forms a heteroazeotrope with the monomers to be purified.

Inert distillation aids used are, for example, hydrocarbons having from 8 to 18 carbon atoms in the molecule or mixtures therof. The hydrocarbons are preferably saturated and can be linear or branched. Particularly preferred distillation aids are saturated hydrocarbons having from 10 to 15 carbon atoms in the molecule or mixtures thereof. The selection of the hydrocarbons is based to a certain extent on the boiling point of the monomer to be purified. Thus, for example, in the distillation of N-vinylformamide n-dodecane or an isomer mixture of dodecanes is used as distillation aid.

The thermolabile monomers to be purified can contain both higher-boiling and lower-boiling constituents. Thus, for example, crude N-vinylformamide which can be prepared by pyrolysis of formylalaninenitrile and contains up to 40% by weight of formylalaninenitrile can be purified by the process of the present invention.

The thermal separation process within the column is carried out as in a conventional distillation. The composition of the distillate depends essentially on the reflux ratio and on the number of theoretical plates in the column. The number of theoretical plates in the column is, for example, from 10 to 60, preferably from 25 to 40. The reflux ratio is set, for example, in the range from 0.5:1 to 4:1, preferably 1:1 to 2:1. At the top of the column, the azeotrope of thermolabile monomers and distillation aid is condensed and collected in a phase separator in which the separation into two phases occurs. The thermolabile monomers are taken from the separator either continuously or portionwise, likewise the distillation aid which is returned to the column or, if desired, worked up by distillation. Components having higher boiling points than the thermolabile monomers are taken off from the bottom of the column.

The process of the present invention is particularly advantageously employed for purifying N-vinylformamide. The advantage of this process in comparison with known processes for the fractionation of N-vinylformamide is, in particular, that it gives monomer qualities which can be processed into particularly high molecular weight polymers. Thus, for example, water-in-oil emulsion polymerization of N-vinylformamide distilled according to the present invention results in poly-N-vinylformamides having Fikentscher K values of above 240 (measured in 5% strength by weight aqueous sodium chloride solution at 25° C., pH=7 and a polymer concentration of 0.1% by weight). The preparation of polymers of N-vinylformamide having such a high molecular weight is difficult because even a few ppm of impurities can have a considerable effect on the polymerization of N-vinylformamide.

In the process of the present invention, high-boiling by-products are discharged from the bottom of the column together with part of the inert distillation aid and possibly small amounts of thermolabile monomers. The amounts of thermolabile monomers in the column bottoms are, for example, up to 5% by weight and are preferably in the range from 0.01 to 1% by weight. The inert distillation aid from the bottom of the column and also from the distillate after phase separation can either be returned to the column or recovered by means of fractional distillation and used again in the process of the present invention.

EXAMPLE

The column had a diameter of 40 mm and a length of 2000 mm. It contained woven packing of stainless steel having a surface area of 750 m²/m³. The packing of the column corresponded to about 25 theoretical plates. The top of the column was fitted with a condenser operated with water at 20° C. and a phase separator. 660 mm above the vaporizer, 300 g/h of a crude N-vinylformamide which had been preheated to 70° C. were introduced into the column. The crude N-vinylformamide was prepared by pyrolysis of formylalaninenitrile and contained 25% by weight of formylalaninenitrile. 50 g/h of n-dodecane were fed continuously into the bottom of the column. Heat input was by means of a falling film evaporator at the bottom of the column. A pressure of 2 mbar was set at the top of the column. At a reflux ratio of 2:1, about 900 g/h of condensate were obtained; the latter separated into two phases in the phase separator. 225 g/h of N-vinylformamide were obtained as lower (monomer) phase which contained 2% of n-dodecane and 0.1% of unidentified by-product. The upper phase comprised almost 95% of n-dodecane and contained about 5% of N-vinylformamide and less than 0.1% of other unidentified by-products. It was returned to the top of the column as runback.

The materials which were not condensed at a condenser temperature of 20° C. and a pressure of 2 mbar at the top of the column were condensed in a downstream cold trap at −80° C. and discharged separately.

In steady-state operation, about 125 g/h of product, which separated into two phases, were obtained at the bottom of the column at 69° C. and a pressure of 9 mbar. The lower phase (85 g) comprised about 90% of formylalaninenitrile, 2% of n-dodecane and less than 8% of other unidentified by-products. The upper phase comprised about 94% of n-dodecane, 5% of formylalaninenitrile and about 1% of other unidentified by-products.

The monomer phase obtained in the phase separator at the top of the column can be used directly for polymerization. The small amounts of n-dodecane have virtually no adverse effect on the course of the polymerization.

We claim:

1. A process for the continuous distillation of thermolabile monomers under reduced pressure in a column which has a vaporizer at the bottom of the column, comprising
   (a) feeding the thermolabile monomers in vapor or liquid form into the column, and introducing an inert distillation aid comprising an aliphatic hydrocarbon having from 8 to 18 carbon atoms in the molecule or a mixture thereof, which forms a heteroazeotrope with said thermolabile monomers, into the vaporizer at the bottom of the column, wherein the thermolabile monomers are introduced into the column separate from the inert distillation aid or
   (b) feeding an emulsion of said thermolabile monomers and said inert distillation aid which forms a heteroazeotrope with said thermolabile monomers, into the vaporizer at the bottom of the column or into the column,
   (c) condensing the heteroazeotrope at the top of the column and separating it in a phase separator, such that components having a higher boiling point than the thermolabile monomers collect in a liquid phase in the column, taking off the thermolabile monomers and returning the distillation aid to the column and optionally working it up by distillation and
   (d) discharging said components having a higher boiling point than the thermolabile monomers which have collected in the liquid phase in the column, from the bottom of the column.

2. A process as claimed in claim 1, wherein the pressure at the top of the column during the distillation is from 0.1 to 100 mbar.

3. A process as claimed in claim 1, wherein the aliphatic hydrocarbon contains from 10 to 15 carbon atoms in the molecule or a mixture thereof.

4. A process as claimed in claim 1, wherein the aliphatic hydrocarbon used is dodecane.

5. A process as claimed in claim 1, wherein the thermolabile monomers used are N-vinylcarboxamides.

6. A process as claimed in claim 1, wherein the thermolabile monomer used is N-vinylformamide.

7. A process as claimed in claim 1, wherein the thermolabile monomer used is N-vinylpyrrolidone.

* * * * *